United States Patent [19]

Abdulla et al.

[11] Patent Number: 4,600,430

[45] Date of Patent: Jul. 15, 1986

[54] PYRIDINYLIMIDAZOLIDINONE COMPOUNDS

[75] Inventors: Riaz F. Abdulla, Greenfield; Jack G. Samaritoni, Knightstown, both of Ind.

[73] Assignee: Eli Lilly and Company, Indianapolis, Ind.

[21] Appl. No.: 704,236

[22] Filed: Feb. 22, 1985

[51] Int. Cl.$^4$ .................... A01N 43/40; C70D 401/04
[52] U.S. Cl. ........................................ 71/92; 546/278
[58] Field of Search ............................ 546/278; 71/92

[56] References Cited

U.S. PATENT DOCUMENTS

| | | | |
|---|---|---|---|
| 3,542,798 | 11/1970 | Doebel et al. | 260/295 |
| 3,646,206 | 2/1972 | Doebel et al. | 424/263 |
| 3,723,455 | 3/1973 | Chupp | 260/309.6 |
| 3,876,657 | 4/1975 | Actony | 260/309.7 |
| 3,990,883 | 11/1976 | Clapot et al. | 71/98 |
| 4,093,444 | 6/1978 | Clapot et al. | 71/92 |
| 4,099,955 | 7/1978 | Clapot et al. | 71/98 |
| 4,268,679 | 5/1981 | Lavanish | 548/247 |
| 4,302,239 | 11/1981 | Lavanish | 71/88 |
| 4,314,844 | 2/1982 | Swithenbank | 71/92 |
| 4,354,030 | 10/1982 | Burow et al. | 548/247 |
| 4,399,137 | 8/1983 | Steiner et al. | 424/250 |
| 4,426,527 | 1/1984 | Lavanish | 548/133 |
| 4,474,962 | 10/1984 | Wepplo | 546/167 |
| 4,507,145 | 3/1985 | Lavanish | 71/92 |
| 4,510,151 | 4/1985 | Lee | 514/341 |

FOREIGN PATENT DOCUMENTS

| | | |
|---|---|---|
| 91596 | 10/1983 | European Pat. Off. . |
| 106962 | 5/1984 | European Pat. Off. . |
| 133310 | 2/1985 | European Pat. Off. . |
| 3237482 | 10/1982 | Fed. Rep. of Germany . |
| 52-031083 | 3/1977 | Japan . |
| 2079283 | 1/1982 | United Kingdom . |
| 2119252 | 11/1983 | United Kingdom . |

OTHER PUBLICATIONS

Abu-Ouf, A., et al. "Nitropyridine Derivatives. 1. Synthesis of 1-(5-nitro-2-pyridyl)-2-Imidazolidinone and Imidazolidinethione", *Drug Res.*, 1(1), 183–188 (1968).
Bianchi, M., et al. "Compounds with Antiulcer and Antisecretory Activity. II. 3-Heteroaryl-Benzimidazolin-2-Ones", *Eur. J. Med. Chem.-Chim. Ther.*, 18(6), 495–500 (1983).
Nagarajan, K., et al. "Nitroimidazoles: Part XIX-Structure-Activity Relationships", *Indian J. Chem., Sect. B*, 23B(4), 342–362 (1984).
Nagarajan, K. "Nitroimidazoles . . . Imidazolidinones", *Indian J. Chem.*, 21B(10), 928–940 (1982).
U.S. Ser. No. 631,555, filed 7/17/84.
U.S. Ser. No. 734,365, filed 5/15/85.
Baskakov et al., CA. 83 127347n.

*Primary Examiner*—Jane T. Fan
*Attorney, Agent, or Firm*—Kathleen R. S. Page; Arthur R. Whale

[57] ABSTRACT

This invention discloses novel pyridinylimidazolidinone compounds, which are useful as herbicides.

12 Claims, No Drawings

PYRIDINYLIMIDAZOLIDINONE COMPOUNDS

BACKGROUND OF THE INVENTION

This invention belongs to the field of agricultural chemistry and provides a class of new herbicidal compounds, herbicidal methods, and formulations making use of the compounds.

SUMMARY OF THE INVENTION

This invention provides pyridinylimidazolidinone compounds of the formula (I):

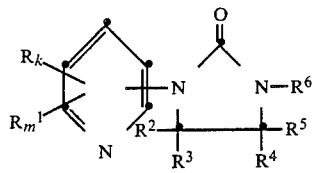

(I)

wherein
R is nitro, cyano, $C_1-C_6$ alkylthio, $C_1-C_6$ alkylsulfinyl, $C_1-C_6$ alkylsulfonyl, $C_3-C_6$ cycloalkyl, $C_3-C_6$ cycloalkenyl,

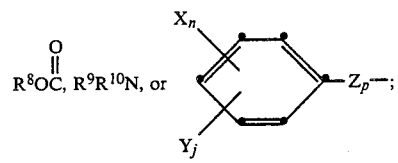

wherein
$R^8$ is hydrogen, $C_1-C_6$ alkyl, or an alkali metal ion;
$R^9$ is hydrogen, $C_1-C_6$ alkyl, or phenyl;
$R^{10}$ is hydrogen or $C_1-C_6$ alkyl;
X is halogen, $C_1-C_6$ alkyl, $C_1-C_6$ alkoxy, or halo($C_1-C_6$ alkyl);
Y is nitro or cyano; and
Z is O, $CH_2$, $CH_2O$, $$\overset{O}{\underset{}{\overset{\|}{C}}}, \text{ or } \overset{O_h}{\underset{}{\overset{\|}{S}}};$$

$R^1$ is halogen, $C_1-C_6$ alkyl, $C_2-C_6$ alkenyl, $C_2-C_6$ alkynyl, $C_1-C_6$ alkoxy, or halo($C_1-C_6$ alkyl);
$R^2$ is hydrogen, hydroxy, $C_1-C_6$ alkyl, $C_1-C_6$ alkoxy, or

wherein
$R^7$ is $C_1-C_6$ alkyl, $C_2-C_6$ alkenyl, $C_2-C_6$ alkynyl, $C_1-C_6$ alkoxy, $C_3-C_6$ cycloalkyl, halogen, naphthyl, $R^9R^{10}N$, or

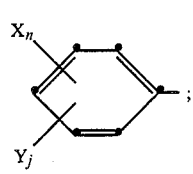

$R^3$ is hydrogen or $C_1-C_6$ alkyl;

$R^4$ is hydrogen, hydroxy, $C_1-C_6$ alkyl, $C_2-C_6$ alkenyl, $C_1-C_6$ alkoxy, or

or together $R^3$ and $R^4$ form a double bond;
$R^5$ is hydrogen or $C_1-C_6$ alkyl;
$R^6$ is hydrogen, $C_1-C_6$ alkyl, $C_1-C_6$ alkoxy, $C_2-C_6$ alkenyl, $C_3-C_6$ cycloalkyl, allyl, or

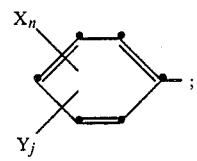

h, j, and k are independently integers from 0 to 2;
m and n are independently integers from 0 to 4;
wherein
the sum of k and m cannot be greater than 4, and each occurrence of the sum of j and n cannot be greater than 5; and
p is an integer from 0 to 1.

Also provided by this invention are methods of use for these compounds as herbicides. Further provided are formulations comprising the pyridinylimidazolidinone compounds and agriculturally-acceptable carriers therefor.

DETAILED DESCRIPTION OF THE INVENTION

In addition to the compounds of formula (I), there is also provided a preferred group of compounds wherein:
$R^1$ is halogen, $C_1-C_6$ alkyl, or halo($C_1-C_6$ alkyl);
$R^2$ is hydrogen, hydroxy or

wherein $R^7$ is $C_1-C_6$ alkyl or

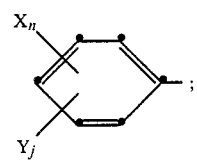

$R^4$ is hydrogen or hydroxy;
$R^6$ is hydrogen or $C_1-C_6$ alkyl;
m and n are from 0 to 2 and j and k are 0.

A more preferred group of compounds include those wherein:
$R^1$ is halogen or $C_1-C_4$ alkyl;
$R^2$ is hydroxy;
$R^3$, $R^4$, and $R^5$ are hydrogen; and
$R^6$ is methyl.

Some of the preferred compounds of this invention are:
3-[4-(1,1-dimethylethyl)-2-pyridinyl]-4-hydroxy-1-methyl-2-imidazolidinone;
3-(5-chloro-2-pyridinyl)-4-hydroxy-1-methyl-2-imidazolidinone;

4-hydroxy-3-(4-methyl-2-pyridinyl)-1-methyl-2-imidazolidinone; and 3-(5-bromo-2-pyridinyl)-4-hydroxy-1-methyl-2-imidazolidinone.

The following defines the various terms used in this application.

The term "$C_1$–$C_6$ alkyl" refers to straight and branched aliphatic groups of one to six carbon atoms including ethyl, propyl, isopropyl (1-methylethyl), butyl, methyl, isobutyl (2-methylpropyl), sec-butyl (1-methylpropyl), tert-butyl (1,1-dimethylethyl), pentyl, isopentyl (3-methylbutyl), sec-pentyl (1-methylbutyl), 1,1-dimethylpropyl, 1,2-dimethylpropyl, neopentyl (2,2-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like. The term "$C_1$–$C_4$ alkyl" is also included in this definition.

The term "$C_2$–$C_6$ alkenyl" refers to unsaturated aliphatic groups of two to six carbon atoms, wherein one carbon to carbon double bond exists in the group, and includes ethenyl, propenyl, 1-butenyl, 2-butenyl, 2-methylpropenyl, 1-pentenyl, 2-pentenyl, 3-pentenyl, 3-methyl-1-butenyl, 2-methyl-2-butenyl, 1-hexenyl, 2-hexenyl, 3-hexenyl, 2,3-dimethyl-2-butenyl, and the like.

The term "$C_2$–$C_6$ alkynyl" refers to unsaturated aliphatic group of two to six carbon atoms, wherein one carbon to carbon triple bond exists in the group, and includes ethynyl, propynyl, butynyl, pentynyl, hexynyl, and the like.

The term "$C_1$–$C_6$ alkoxy" refers to aliphatic groups of one to six carbon atoms attached to the remainder of the molecule by an oxygen atom, such as methoxy, ethoxy, propoxy, butoxy, and the like.

The term "$C_1$–$C_6$ alkylthio" refers to aliphatic groups of one to six carbon atoms attached to the remainder of the molecule by a sulfur atom, such as methylthio, ethylthio, propylthio, and the like.

The term "$C_1$–$C_6$ alkylsulfinyl" refers to aliphatic groups of one to six carbon atoms attached to the remainder of the molecule by a sulfinyl group, such as methylsulfinyl, ethylsulfinyl, propylsulfinyl, and the like.

The term "$C_1$–$C_6$ alkylsulfonyl" refers to aliphatic groups of one to six carbon atoms attached to the remainder of the molecule by a sulfonyl group, such as methylsulfonyl, ethylsulfonyl, and the like.

The term "$C_3$–$C_6$ cycloalkyl" refers to saturated aliphatic rings of three to six carbon atoms, such as cyclopropyl, cyclobutyl, cyclopentyl, and cyclohexyl.

The term "$C_3$–$C_6$ cycloalkenyl" refers to unsaturated aliphatic rings of three to six carbon atoms, such as cyclopropenyl, cyclobutenyl, cyclopentenyl, cyclohexenyl, and the like.

The halogens include bromine, chlorine, fluorine, and iodine.

The term "halo($C_1$–$C_6$ alkyl)" refers to straight and branched aliphatic groups of one to six carbon atoms which have one or more halogen atoms attached to the alkyl, such as trifluoromethyl.

The term "allyl" refers to the group —$CH_2CH=CH_2$.

The term "alkali metal ion" refers to the cation of lithium, sodium, potassium, and the like.

PREPARATION OF THE COMPOUNDS OF FORMULA (I)

The processes for making the pyridinylimidazolidinone compounds of formula (I) are outlined below.

Preparation 1: Preferred

The compounds of formula (I) are preferably prepared by cyclization of a pyridinylurea of the formula:

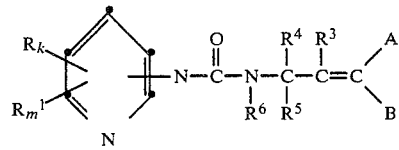

using ozonation, followed by reduction, wherein R, $R^1$, $R^3$, $R^4$, $R^5$, $R^6$, k and m are defined as above, and A and B are $C_1$–$C_6$ alkyl groups, such as methyl, ethyl, propyl, or substituted phenyl, and the like. This reaction can be carried out by oxidizing the urea starting compound with ozone. Ozone may be supplied to the process in the usual way: diluted with air as it is formed in typical ozonators. It has been found that no particular excess of ozone is necessary, if the air-ozone mixture is efficiently dispersed in the reaction mixture with good agitation. Chemists usually monitor reactions with ozone by testing the off-gas from the reactor with an indicator, such as a dye or starch/iodine paper, and adjusting the addition rate of the ozone to minimize wasting it. Completion of the reaction is easily observed in the same way, because it is signaled by a sudden increase in the concentration of ozone leaving the reactor.

No particular precautions need be observed in the ozone reaction, except that reaction mixtures have often been observed to foam vigorously as the reaction proceeds. Adequate head space in the reactor must be allowed to accommodate foaming; small amounts of antifoam materials such as silicone may be used.

After the oxidation with ozone is complete, a sufficient amount of reducing agent is added to reduce residual ozone dissolved in the mixture, and to reduce the oxidized intermediate itself. In general, from about 1.1 to about 2.0 equivalents of reducing agent should be added per mole of starting compound. The usual types of reducing agents are used for the reduction. It is unnecessary to use catalytic or electrolytic reduction; inexpensive reducing agents, such as $C_1$–$C_4$ dialkyl sulfides, thiosulfate salts, sulfite salts, hydrosulfite salts, phosphite salts, alkali metal iodides, sulfur dioxide, stannous chloride, zinc or magnesium metal, formaldehyde, and the like, are entirely satisfactory. Dialkyl sulfides, especially dimethyl sulfide, are most preferred.

The process is carried out in an organic solvent, which is inert to the oxidizing and reducing agents. Solvents, such as halogenated alkanes, lower alkanols, alkyl ketones, aromatics, esters, and the like, may be used as is convenient in the circumstances. It is preferable to use a water-immiscible solvent, or a substantial amount (at least enough to dissolve the product) of a water-immiscible solvent, if a solvent mixture is used, to facilitate isolation of the product. Relatively minor amounts of lower alkanoic acids or water may also be used in the mixture. Useful specific solvents include, for example, methylene chloride, 1,2-dichloroethane, methanol, isopropanol, methyl ethyl ketone, methyl isobutyl ketone, diisopropyl ketone, ethyl acetate, 1,1,2-trichloroethane, benzene, toluene, propyl butyrate, ethylbenzene, and the like. Particularly preferred solvents are mixtures of halogenated alkanes and alkanols, especially methylene chloride/methanol mixtures.

Both the oxidation and reduction steps are preferably carried out in the same solvent, by merely adding the reducing agent to the mixture.

The oxidation step is preferably carried out at a relatively low temperature, in the range of from about $-100°$ to about $-50°$ C. Good results are obtained, however, at temperatures in the broad range from about $-100°$ C. to about the ambient temperature. It is not necessary to use a reduced temperature during the reduction step, however, and the mixture may be allowed to warm to ambient, or even to be moderately heated in the range from about the ambient temperature to about 90° C., while the reducing agent is added and the reduction is carried out.

Both steps of the process are quite rapid. The speed of the oxidation step is apparently limited only by the speed with which the ozone can be dispersed and dissolved in the reaction mixture.

Preparation 2

Most of the pyridinylimidazolidinone compounds provided by this invention also can be prepared by the cyclization of a suitably substituted pyridinylurea of the formula:

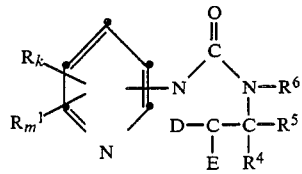

wherein

D and E are $C_1$–$C_6$ alkoxy, such as methoxy, ethoxy, propoxy, and the like.

The cyclization of the urea intermediate can be accomplished by simply heating the intermediate in the presence of an acid. Commonly used acids include mineral acids, such as hydrochloric, hydrobromic, sulfuric, phosphoric, nitric, and related acids. Organic acids, such as acetic acid, can also be utilized if desired. The amount of acid commonly employed to effect the cyclization is about an equimolar amount or an excess, and routinely the reaction is simply carried out in a dilute aqueous acid solution having an acid concentration of about 0.5 to about 5 percent by weight. If desired, the cyclization reaction can be carried out in a solvent medium other than water, such as dioxane, dimethylsulfoxide (DMSO), dimethylformamide (DMF), and the like, with an equimolar or excess amount of suitable acid added. The cyclization reaction generally is substantially complete within about 10 to about 90 minutes when carried out at an elevated temperature of about 40° to about 100° C. The reaction provides a pyridinylimidazolidinone, which is readily isolated by cooling the reaction mixture, for instance to 0° to about 5° C., and then collecting the precipitate. The precipitated pyridinylimidazolidinone can be further purified, if desired, by conventional means, including chromatography and crystallization from common solvents, such as ethanol, acetone, dioxane, water, and the like.

Preparation 3

Some compounds of this invention can also be prepared by condensation of a halopyridine and an imidazolidinone.

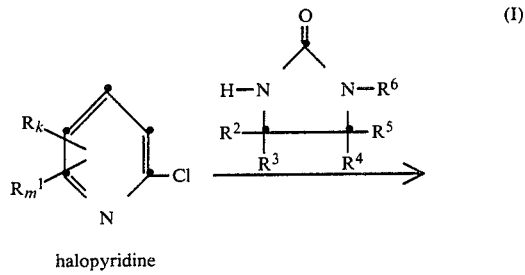

halopyridine

Commonly a base is used to insure deprotonation of the imidazolidinone, such a base includes sodium hydride. The reaction is carried out in an inert solvent, such as tetrahydrofuran (THF), DMF, toluene, and the like at temperatures from 25° C. to 100° C. for about one half to 24 hours. Upon completion of the reaction, dilute hydrochloric acid or water is added and the organic phase is dried and concentrated. The resulting material can be purified by recrystallization or chromatography.

Preparation 4

Pyridinylimidazolidinones wherein $R^2$ and $R^4$ are hydroxy can be prepared by reacting a pyridinylurea with glyoxal to form the pyridinyl-4,5-dihydroxyimidazolidinone. Typically, the glyoxal is in the form of an aqueous solution, which has been adjusted to a pH of between 7 and 8 with a suitable inorganic base, such as sodium hydroxide, potassium hydroxide, and the like. The reaction of the urea and glyoxal is carried at temperatures from 15° to 80° C., preferably from 20° to 40° C., for a period of 10 to 24 hours, preferably for about 18 hours. In addition, an inert organic solvent, such as THF, ethanol, and the like, is used.

The pyridinylimidazolidinones thus described are useful not only as herbicides, but also as intermediates in the synthesis of other imidazolidinones of this invention.

Preparation 5

The pyridinyl-4-hydroxyimidazolidinones are useful in the preparation of those imidazolidinones of the above general formula wherein $R^2$ is

$OCR^7$.

For example, the pyridinyl-4-hydroxyimidazolidinones of the invention are readily acylated with an acylating agent, such as an acid halide. Commonly used acylating agents include acetyl chloride, butyryl iodide, benzoyl chloride, hexanoyl bromide, and the like. Other acylating agents commonly employed include anhydrides, such as acetic anhydride, acetic formic anhydride, propanoic formic anhydride, and the like.

The acylation of a pyridinyl-4-hydroxyimidazolidinone can be accomplished by reacting about equimolar quantities of a 4-hydroxyimidazolidinone and the acylating agent. An excess of the acylating agent can be employed if desired. Sodium hydride is added to the reaction in order to generate the corresponding alkoxide.

The reaction typically is conducted in a solvent, such as benzene, acetone, THF, methylene chloride, chloroform, or the like. The acylation reaction is generally substantially complete after about 2 to about 24 hours when carried out at a temperature of about −20° to about 80° C. The acylated product can be isolated by simply removing the reaction solvent, for instance, by evaporation under reduced pressure. The acylated imidazolidinone can be purified, if needed, by conventional means, including washing with dilute acid and dilute base, chromatography, crystallization, and the like.

Preparation 6

Imidazolones of the invention, (i.e. compounds of the above formula wherein $R^3$ and $R^4$ together form a double bond) are preferably prepared by dehydrating a hydroxyimidazolidinone.

Such dehydration can be effected by reacting the hydroxyimidazolidinone with an acid, such as a mineral acid, or preferably with an equimolar amount or slight excess of a halogenating agent, such as thionyl chloride. For example, reaction of a 4- or 5-hydroxyimidazolidinone with about an equimolar amount of thionyl chloride in a solvent such as chloroform or methylene chloride for about 1 to about 24 hours at a temperature of about 0° to about 50° C. provides the corresponding imidazolone. The product can be recovered by simply removing the reaction solvent, for instance by evaporation, and further purification can be achieved, if desired, by routine procedures, such as crystallization from common solvents like acetone or diethyl ether.

Preparation 7

Halide groups on the pyridine ring of the compounds of this invention can be removed to form the unsubstituted pyridazine by a slight pressure of hydrogen gas in the presence of a metal catalyst, such as platinum, palladium on carbon, and Raney nickel.

PREPARATION OF INTERMEDIATES

Pyridinylurea intermediates can be prepared by any of several procedures. In a typical procedure, a substituted pyridine is reacted with a haloformate, such as phenyl chloroformate, to give an N-pyridinyl carbamate, which when reacted with a suitably substituted ethylamine gives the pyridinylurea.

The reaction of a haloformate, such as phenyl chloroformate, and a pyridinylamine generally is carried out by combining a slight excess of haloformate with the pyridine in an organic solvent, such as triethylamine or pyridine, and stirring the mixture for about 1 to about 24 hours at a temperature of about 0° to about 30° C. The product of the reaction, a pyridinyl carbamate, is generally isolated by acidifying the reaction mixture, for instance by the addition of a mineral acid, such as hydrochloric acid or sulfuric acid, and collecting by filtration the precipitate which forms. The carbamate normally needs no further purification, but if desired it can be crystallized from common solvents, such as benzene, acetone, ethyl acetate, and the like.

The carbamate and the ethylamine generally are combined in a mutual organic solvent, such as toluene, benzene, and THF. The reactants can be utilized in about equimolar amounts, or if desired the ethylamine derivative can be employed in excess. The reaction routinely is substantially complete within about 2 to about 5 hours when carried out at a temperature of about 50° to about 100° C. Isolation of the product, a pyridinylurea intermediate, usually is accomplished by simply removing the reaction solvent, for instance, by evaporation under reduced pressure. In some instances, the product is washed with base. The urea can be further purified, if needed, by routine methods, including recrystallization and chromatography.

An alternative procedure for preparing the intermediates of the invention comprises reacting a suitably substituted ethylamine with a pyridinyl isocyanate. The isocyanate is conveniently prepared by reacting a pyridine with phosgene in the presence of an acid, such as hydrochloric acid, to give the corresponding pyridinylcarbamoyl chloride. The latter compound undergoes dehydrohalogenation in situ to provide the corresponding pyridinyl isocyanate. (The isocyanate is formed as the dimer or trimer.)

The reaction of an ethylamine with a pyridinyl isocyanate generally is carried out by combining approximately equimolar quantities of the reactants in a suitable solvent, such as benzene, toluene, or THF. The reaction normally is complete within about 2 to about 5 hours when carried out at a temperature of about 50° to about 100° C. Isolation of the product generally is achieved by simply removing the reaction solvent by evaporation under reduced pressure. Further purification, if needed, can be accomplished by crystallization, chromatography, or similar conventional methods.

The following examples are illustrative of this invention. However, these examples are not to be construed as limitations on the invention. The temperatures are reported in degrees Celsius.

EXAMPLE 1

3-[4-(1,1-Dimethylethyl)-2-pyridinyl]-4-hydroxy-1-methyl-2-imidazolidinone

To a solution of 3.36 g (0.0136 mole) of N'-[4-(1,1-dimethylethyl)-2-pyridinyl]-N-methyl-N-(2-propenyl-)urea in 180 ml of methylene chloride and 20 ml of methanol was added a trace of Sudan III (pH indicator). Using a dry ice-acetone bath, the solution was lowered to a temperature of about −60° to −50° and an ozone-/air mixture was bubbled in through a fritted glass tube.

After about 11 minutes, when the indicator was colorless, air was bubbled in to remove any dissolved ozone and then 2.0 ml (1.7 g, 0.027 mole, 2.0 equivalents) of methyl sulfide was added. The solution was diluted with methylene chloride. After washing with three 80-ml portions of water, the solution was dried with magnesium sulfate.

The solution was concentrated, affording 3.5 g of an oil. The oil was chromatographed on dry pack silica gel using methylene chloride as the eluant. The product was collected and weighed 2.5 g (74%). The molecular weight was 249.30. NMR, IR, and mass spectra were consistent with the structure of the desired product.

The following elemental analysis was obtained:
Calculated for $C_{13}H_{19}N_3O_2$: Theory: C, 62.63; H, 7.68; N, 16.85; Found: C, 61.99; H, 7.93; N, 16.63.

The following examples were prepared using the general procedure of Example 1.

EXAMPLE 2

3-(5-Chloro-2-pyridinyl)-4-hydroxy-1-methyl-2-imidazolidinone

Yield = 1.26 g (52%)
Melting Point (MP) = 146°–149°

NMR, IR, and mass spectra were consistent with the structure of the desired product.
MW=227.65
Calculated for $C_9H_{10}ClN_3O_2$: Theory: C, 47.48; H, 4.43; N, 18.46; Found: C, 47.73; H, 4.39; N, 18.31.

EXAMPLE 3

4-Hydroxy-3-(6-methyl-2-pyridinyl)-1-methyl-2-imidazolidinone

Yield=0.81 g (28%)
MP=110°–112°
NMR, IR, and mass spectra were consistent with the structure of the desired product.
MW=207.22
Calculated for $C_{10}H_{13}N_3O_2$: Theory: C, 57.96; H, 6.32; N, 20.28; Found: C, 57.81; H, 6.42; N, 20.16.

EXAMPLE 4

4-Hydroxy-3-(4-methyl-2-pyridinyl)-1-methyl-2-imidazolidinone

Yield=2.30 g (50%)
MP=126.5°–128.5°
NMR, IR, and mass spectra were consistent with the structure of the desired product.
MW=207.22
Calculated for $C_{10}H_{13}N_3O_2$: Theory: C, 57.96; H, 6.32; N, 20.28; Found: C, 58.18; H, 6.35; N, 20.25.

EXAMPLE 5

3-(4,6-Dimethyl-2-pyridinyl)-4-hydroxy-1-methyl-2-imidazolidinone

Yield=0.40 g (37%)
MP=100°–101°
NMR, IR, and mass spectra were consistent with the structure of the desired product.
MW=221.25
Calculated for $C_{11}H_{15}N_3O_2$: Theory: C, 59.71; H, 6.83; N, 18.99; Found: C, 59.93; H, 6.88; N, 18.92.

EXAMPLE 6

4-Hydroxy-1-methyl-3-(2-pyridinyl)-2-imidazolidinone

Yield=1.50 g (49%)
MP=126°–127°
NMR, IR, and mass spectra were consistent with the structure of the desired product.
MW=193.20
Calculated for $C_9H_{11}N_3O_2$: Theory: C, 55.95; H, 5.74; N, 21.75; Found: C, 56.23; H, 6.01; N, 21.96.

EXAMPLE 7

3-(5-Bromo-2-pyridinyl)-4-hydroxy-1-methyl-2-imidazolidinone

Yield=1.96 g (40%)
MP=148° (dec)
NMR, IR, and mass spectra were consistent with the structure of the desired product.
MW=272.11
Calculated for $C_9H_{10}BrN_3O_2$: Theory: C, 39.73; H, 3.70; N, 15.44; Found: C, 39.77; H, 3.43; N, 15.57.

EXAMPLE 8

4-Hydroxy-1-methyl-3-(5-nitro-2-pyridinyl)-2-imidazolidinone

Yield=1.39 g (49%)
MP=218°–218.5° (dec)
NMR and mass spectra were consistent with the structure of the desired product.
MW=238.20
Calculated for $C_9H_{10}N_4O_4$: Theory: C, 45.38; H, 4.23; N, 23.52; Found: C, 45.24; H, 3.98; N, 23.39.

EXAMPLE 9

4-Hydroxy-1-methyl-3-(3-nitro-2-pyridinyl)-2-imidazolidinone

Yield=0.86 g (66%)
MP=181°–183° (dec)
NMR and mass spectra were consistent with the structure of the desired product.
MW=238.21
Calculated for $C_9H_{10}N_4O_4$: Theory: C, 45.38; H, 4.23; N, 23.52; Found: C, 45.62; H, 4.08; N, 23.41.

EXAMPLE 10

3-(3,5-Dichloro-2-pyridinyl)-4-hydroxy-1-methyl-2-imidazolidinone

Yield=0.45 g (37%)
MP=178°–181° (dec)
NMR and mass spectra were consistent with the structure of the desired product.
MW=262.09
Calculated for $C_9H_9Cl_2N_3O_2$: Theory: C, 41.24; H, 3.46; N, 16.03; Found: C, 41.45; H, 3.20; N, 16.24.

EXAMPLE 11

3-(6-Ethoxy-3-nitro-2-pyridinyl)-4-hydroxy-1-methyl-2-imidazolidinone

Yield=0.40 g (11%)
MP=163.5°–165.5°
NMR and mass spectra were consistent with the structure of the desired product.
Calculated for $C_{11}H_{14}N_4O_5$: Theory: C, 46.81; H, 5.00; N, 19.85; Found: C, 47.07; H, 5.17; N, 19.59.

EXAMPLE 12

3-(3-Cyano-2-pyridinyl)-4-hydroxy-1-methyl-2-imidazolidinone

Yield=1.76 g (65%)
MP=184°–185° (dec)
NMR, IR, and mass spectra were consistent with the structure of the desired product.
MW=218.21
Calculated for $C_{10}H_{10}N_4O_2$: Theory: C, 55.04; H, 4.62; N, 25.67; Found: C, 54.90; H, 4.70; N, 25.46.

EXAMPLE 13

4-Hydroxy-3-(3-methyl-2-pyridinyl)-1-methyl-2-imidazolidinone

Yield=0.64 g (30%)
MP=100°–103°
NMR and mass spectra were consistent with the structure of the desired product.
MW=207.22
Calculated for $C_{10}H_{13}N_3O_2$: Theory: C, 57.96; H, 6.32; N, 20.28; Found: C, 57.71; H, 6.04; N, 20.08.

EXAMPLE 14

4-Hydroxy-3-(5-trifluoromethyl-2-pyridinyl)-1-methyl-2-imidazolidinone

Yield=0.48 g (56%)
MP=156°–158.5°

NMR and mass spectra were consistent with the structure of the desired product.
MW=261.20
Calculated for $C_{10}H_{10}F_3N_3O_2$: Theory: C, 45.98; H, 3.86; N, 16.09; Found: C, 45.72; H, 3.67; N, 15.92.

EXAMPLE 15

3-[3-Cyano-6-(1,1-dimethylethyl)-2-pyridinyl]-4-hydroxy-1-methyl-2-imidazolidinone Yield=0.70 g (88%)
MP=144°–148°
NMR and mass spectra were consistent with the structure of the desired product.
MW=274.31
Calculated for $C_{14}H_{18}N_4O_2$: Theory: C, 61.30; H, 6.61; N, 20.42; Found: C, 61.06; H, 6.65; N, 20.16.

EXAMPLE 16

3-(5-Benzoyl-2-pyridinyl)-4-hydroxy-1-methyl-2-imidazolidinone

Yield=0.92 g (44%)
MP=133°–134°
NMR and mass spectra were consistent with the structure of the desired product.
MW=297.30
Calculated for $C_{16}H_{15}N_3O_3$: Theory: C, 64.64; H, 5.09; N, 14.13; Found: C, 64.86; H, 4.91; N, 13.83.

EXAMPLE 17

4-Hydroxy-3-(5-methyl-2-pyridinyl)-1-methyl-2-imidazolidinone

Yield=2.02 g (44%)
MP=145°–146.5°
NMR, IR, and mass spectra was consistent with the structure of the desired product.
MW=207.22
Calculated for $C_{10}H_{13}N_3O_2$: Theory: C, 57.96; H, 6.32; N, 20.28; Found: C, 57.88; H, 6.12; N, 20.07.

TERRESTRIAL HERBICIDAL METHOD

Also provided by this invention is a method of inhibiting the growth of unwanted vegetation which comprises contacting the vegetation or the soil in which the vegetation is growing with a herbicidally-effective amount of a compound of the formula (I). The pyridinylimidazolidinones provided by this invention exhibit terrestrial herbicidal activity and accordingly are useful in the control and elimination of unwanted vegetative growth.

The herbicides of the invention are effective terrestrially in both preemergent and postemergent control of a wide variety of grasses, broadleaf weeds, and sedges. Commonly encountered unwanted terrestrial vegetation, which is subject to control with the herbicidal compounds of this invention include:

Wild Oat (*Avena fatua*)
Catchweed Bedstraw (*Galium aparine*)
Scentless Mayweed (*Matricaria inodora*)
Ladysthumb (*Polygonum persicaria*)
Common Chickweed (*Stellaria media*)
Ivyleaf Speedwell (*Veronica hederaefolia*)
Blackgrass (*Alopecurus myosuroides*)
Chrysanthemum (Chrysanthemum spp.)
Common Purslane (*Portulaca oleracea*)
Sida (Sida spp.)
Bristly Starbur (*Acanthospermum hispidum*)
Goosegrass (*Eleusine indica*)
Smooth Pigweed (*Amaranthus hybridus*)
Alexandergrass (*Brachiaria plantaginea*)
Tall Morningglory (*Ipomoea purpurea*)
Common Lambsquarter (*Chenopodium album*)
Green Smartweed (*Polygonum scabrum*)
Green Foxtail (*Setaria viridis*)
Redroot Pigweed (*Amaranthus retroflexus*)
Wild Buckwheat (*Polygonum convolvulus*)
Brazil Calalilly (*Richardia brasiliensis*)
Natal Grass (*Rhynchelytrum roseum*)
Ryegrass (*Lolium rigidum*)
Kapeweed (*Cryptostemma calendula*)
Purple Loosestrife (*Lythrum salicaria*)
Wild Radish (*Raphanus raphanistrum*)
Wireweed (*Polygonum aviculare*)
Henbit (*Lamium amplexicaule*)
Wild Mustard (*Brassica kaber*)
Barnyard Grass (*Echinochloa crus-galli*)
Foxtail Millet (*Setaria italica*)
Velvetleaf (*Abutilon theophrasti*)
Indian Mustard (*Brassica juncea*)
Birdseye Speedwell (*Veronica persica*)
Canada Thistle (*Cirsium arvense*)
Wild Chamomile (*Matricaria chamomilla*)
Annual Bluegrass (*Poa annua*)
Buttercup (Ranunculus spp.)
Field Speedwell (*Veronica agrestis*)
Field Violet (*Viola arvensis*)
Field Pennycress (*Thlaspi arvense*)
Wild Violet (*Viola tricolor*)
Shirley Poppy (*Papaver rhoeas*)
Field Poppy (*Papaver dubium*)
Foolsparsley (*Aethusa cynapium*)
Field Chickweed (*Cerastium arvense*)
Southern Sandbur (*Cenchrus echinatus*)
Large Crabgrass (*Digitaria sanguinalis*)
Cheat (*Bromus secalinus*)
Morningglory (Ipomea spp.)
Common Ragweed (*Ambrosia artemisiifolia*)
Common Milkweed (*Asclepias syriaca*)
Giant Foxtail (*Setaria faberi*)
Common Cocklebur (*Xanthium pensylvanicum*)
Spurred Anoda (*Anoda cristata*)
Sicklepod (*Cassia obtusifolia*)
Yellow Nutsedge (*Cyperus esculentus*)
Jimsonweed (*Datura stramonium*)
Prickly Sida (*Sida spinosa*)
Corn Gromwell (*Lithospermum arvense*)
Yellow Foxtail (*Setaria glauca*)
Tansymustard (*Descurainia pinnata*)
Pepperweed (Lepidium spp.)
Bromegrass (Bromus spp.)
Garden Spurge (*Euphorbia hirta*)
Crowfootgrass (*Dactyloctenium aegyptium*)
Florida Beggarweed (*Desmodium tortuosum*)
Spotted Spurge (*Euphorbia maculata*)
Smallflower Morningglory (*Jacquemontia tamnifolia*)
Browntop Millet (*Panicum ramosum*)
Coast Fiddleneck (*Amsinckia intermedia*)
Wild Turnip (*Brassica campestris*)
Black Mustard (*Brassica nigra*)
Shepherdspurse (*Capsella bursa-pastoris*)
Italian Ryegrass (*Lolium multiflorum*)
London Rocket (*Sisymbrium irio*)
Redmaids Rockpurslane (*Calandrinia caulescens*)
Common Groundsel (*Senecio vulgaris*)
Ivyleaf Morningglory (*Ipomoea hederacea*)

Fall Panicum (*Panicum dichotomiflorum*)
Powell Amaranth (*Amaranthus powellii*)
Texas Panicum (*Panicum texanum*)
Hemp Sesbania (*Sesbania exaltata*)
Annual Sowthistle (*Sonchus oleraceus*)
Field Bindweed (*Convolvulus arvensis*)
Erect Knotweed (*Polygonum erectum*)
Venice Mallow (*Hibiscus trionum*)
Zinnia (*Zinnia elegans*)
Nightshade (*Solanum* spp.)

The present compounds have also been found safe on a wide variety of desirable plant species, thereby exhibiting their unique selective capacity. Representative examples of relatively tolerant plant species, depending on the concentration of active ingredient employed and the means of application, include the following:

Corn (*Zea mays*) (Corn is the preferred crop for treatment.)
Wheat (*Triticum aestivum*)
Soybean (*Glycine max*)
Rice (*Oryza sativa*)
Barley (*Hordeum vulgare*)
Cotton (*Gossypium hirsutum*)
Sorghum (*Sorghum vulgare v. saccharatum*)
Sugarcane (*Saccharum officinarum*)
Peanut (*Arachis hypogaea*)
Alfalfa (*Medicago sativa*)
Cucumber (*Cucumis sativus*)
Tomato (*Lycopersicon esculentum*)
Sugar Beet (*Beta vulgaris*)

A test used to evaluate herbicidal efficacy was conducted at a compound concentration of 15 pounds per acre (16.8 kilograms per hectare). In this test a standard sand/soil mixture (1:1) was sterilized and added to separate containers and tomato, large crabgrass, and pigweed seeds were planted by row.

The test compounds were formulated for application by dissolving the compound into a solvent, containing acetone, ethanol, and a blend of anionic and nonionic surfactants. The solvent/compound solution was diluted with deionized water and applied postemergence to some planted containers and preemergence to others. Postemergent treatment was made 11 to 13 days after planting, while preemergent treatment was made one day after planting.

Following treatment the containers were moved to the greenhouse and watered as necessary. Observations were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury, and "5" indicates death to the plant or no seedling emergence.

Table 1, which follows, presents the terrestrial herbicidal activity of the compound at 15 pounds per acre (lb/A).

TABLE 1

| Compound of Example No. | Terrestrial Herbicidal Activity Plant Species | | | | | |
|---|---|---|---|---|---|---|
| | Preemergence | | | Postemergence | | |
| | Tomato | Large Crabgrass | Pigweed | Tomato | Large Crabgrass | Pigweed |
| 1 | 5 | 5 | 5 | 5 | 5 | 5 |
| 2 | 5 | 4 | 4 | 5 | 5 | 5 |
| 6 | 4 | 5 | 5 | 5 | 5 | 5 |
| 7 | 4 | 5 | 5 | 5 | 5 | 5 |
| 8 | 1 | 1 | 1 | 1 | 1 | 1 |
| 9 | 1 | 1 | 1 | 2 | 3 | 1 |

The herbicidal activity of some of the compounds of the present invention was further evaluated at various application rates in a multiple-species greenhouse test. Several additional weed and crop species were utilized to determine the herbicidal activity and selectivity of the test compounds. Lower concentrations of the test compounds were obtained by serial dilution of the above-described formulation with a mixture of the surfactant and deionized water. The compounds were evaluated according to the general procedure outlined above. See Tables 2 and 3.

The following code was used in Tables 2 and 3:

| | |
|---|---|
| A = Corn | N = Large Crabgrass |
| B = Cotton | O = Mustard |
| C = Soybean | P = Pigweed |
| D = Wheat | Q = Ryegrass |
| E = Alfalfa | R = Small Crabgrass |
| F = Sugar Beet | S = Foxtail Millet |
| G = Rice | T = Bindweed |
| H = Cucumber | U = Wild Oat |
| I = Tomato | V = Nutgrass |
| J = Barley | W = Velvetleaf |
| K = Barnyard Grass | X = Jimsonweed |
| L = Lambsquarter | Y = Smartweed |
| M = Cocklebur | Z = Morningglory |
| | a = Zinnia |

Note:
8 lb/A = 8.96 kilograms per hectare (kg/ha)
4 lb/A = 4.48 kg/ha
2 lb/A = 2.24 kg/ha
1 lb/A = 1.12 kg/ha.

TABLE 2

| EX. No. | Rate lbs/A | PLANT SPECIES Pre-emergence | | | | | | | | | | | | | | | | | | | | | | | | | |
|---|---|---|---|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | U | V | W | X | Y | Z | a |
| 1 | .5 | 3 | 2 | 4 | 4 | | 5 | 4 | | 4 | | | | | 5 | 5 | 5 | | 5 | 5 | | 5 | 5 | | 5 | 5 | 5 | 5 |
| | .5 | 1 | 1 | 1 | 1 | 4 | 5 | 3 | 5 | 5 | 5 | 5 | | | 5 | 5 | 5 | | 5 | 3 | | 5 | 5 | | 3 | 5 | | | |
| | .2 | 2 | 1 | 2 | 2 | | 5 | 3 | | 4 | | | | | 5 | 5 | 5 | | 5 | 5 | | 5 | 4 | | 5 | 5 | | | |
| | .2 | 1 | 1 | 1 | 1 | 2 | 5 | 3 | 4 | 1 | 5 | 1 | 5 | | 5 | 5 | 5 | | 5 | 3 | | 5 | 5 | | 1 | 5 | | | |
| | 8 | | | | | | | | | | | 5 | | | 5 | 5 | 5 | | 5 | 5 | | 5 | | | 5 | 5 | | | |
| | 4 | 4 | 5 | 5 | 5 | 5 | 5 | 5 | 5 | 5 | | 5 | 5 | | 5 | 5 | 5 | | 5 | 5 | | 5 | 5 | | 5 | 5 | | | |
| | 2 | 4 | 5 | 5 | 5 | 5 | 5 | 5 | 5 | 5 | | 5 | 5 | | 5 | 5 | 5 | | 5 | 5 | | 5 | 5 | | 5 | 5 | | | |
| | 1 | 3 | 5 | 5 | 5 | | 5 | 4 | | | 5 | | | | 5 | 5 | 5 | | 5 | 5 | | 5 | 5 | | 5 | 5 | | | |
| | 1 | 3 | 2 | 3 | 4 | 5 | 5 | 5 | 5 | 5 | | 5 | 5 | | 5 | 5 | 5 | | 5 | 5 | | 5 | 5 | | 5 | 5 | | | |
| | 1 | 1 | 2 | 2 | 2 | 4 | 5 | 4 | 5 | 5 | | 5 | 5 | | 5 | 5 | 5 | | 5 | 4 | | 5 | 5 | | 4 | 5 | | | |
| 2 | .5 | 1 | 1 | 1 | 1 | 1 | 5 | 2 | 3 | 2 | | 4 | 5 | | 1 | 2 | 5 | | 2 | 1 | | 3 | 4 | | 1 | 2 | | | |
| | .2 | 1 | 1 | 1 | 1 | 1 | 4 | 1 | 3 | 2 | | 3 | 5 | | 1 | 1 | 5 | | 1 | 1 | | 3 | 4 | | 1 | 1 | | | |
| | 8 | | | | | | | | | | | | | 5 | | | | | | | | | | | | | | | |
| | | | | | | | | | | | | | | | | | | | | | | | | | | | | |
| | 4 | 1 | 2 | 3 | 3 | 5 | 5 | 5 | 5 | 5 | | 5 | 5 | | 2 | 5 | 5 | | 5 | 4 | | 5 | 5 | | 3 | 5 | | | |
| | 2 | 1 | 1 | 1 | 1 | 5 | 5 | 4 | 5 | 5 | | 5 | 5 | | 2 | 5 | 5 | | 5 | 4 | | 5 | 5 | | 3 | 5 | | | |

TABLE 2-continued

| EX. No. | Rate lbs/A | A | B | C | D | E | F | G | H | I | J | K | L | M | N | O | P | Q | R | S | T | U | V | W | X | Y | Z | a |
|---|---|---|---|---|---|---|---|---|---|---|---|---|---|---|---|---|---|---|---|---|---|---|---|---|---|---|---|---|
| | 1 | 1 | 1 | 1 | 1 | 5 | 5 | 3 | 4 | 5 | | 4 | 5 | | 1 | 4 | 5 | | 4 | 3 | | 4 | 4 | | | 2 | 4 | |
| | 1 | 1 | 1 | 1 | 1 | 3 | 5 | 2 | 3 | 2 | | 4 | 5 | | 1 | 3 | 5 | | 4 | 1 | | 5 | 4 | | | 1 | 3 | |
| 3 | 8 | | | | | | | | | 3 | | 2 | | | 3 | 3 | 4 | | 2 | 1 | | 4 | | | | 2 | 2 | |
| | 4 | 1 | 1 | 1 | 2 | 2 | 4 | 3 | 3 | 2 | | 2 | 5 | | 3 | 2 | 5 | | 2 | 2 | | 4 | 2 | | | 3 | 3 | |
| | 2 | 1 | 1 | 1 | 1 | 1 | 2 | 1 | 2 | 1 | | 1 | 4 | | 1 | 2 | 4 | | 1 | 2 | | 2 | 1 | | | 2 | 3 | |
| | 1 | 1 | 1 | 1 | 1 | 1 | 1 | 1 | 1 | 1 | | 1 | 3 | | 1 | 1 | 1 | | 1 | 1 | | 1 | 1 | | | 1 | 1 | |
| 4 | 8 | | | | | | | | | 5 | | 5 | | | 5 | 5 | 5 | | 5 | 5 | | 5 | | | | 5 | 5 | |
| | 4 | 2 | 5 | 4 | 3 | 5 | 5 | 5 | 5 | 5 | | 5 | 5 | | 5 | 5 | 5 | | 5 | 5 | | 5 | 5 | | | 5 | 5 | |
| | 2 | 2 | 3 | 2 | 3 | 5 | 5 | 4 | 5 | 5 | | 5 | 5 | | 5 | 5 | 5 | | 5 | 5 | | 5 | 5 | | | 4 | 5 | |
| | 1 | 2 | 2 | 2 | 2 | 4 | 5 | 4 | 5 | 5 | | 5 | 5 | | 5 | 4 | 5 | | 5 | 4 | | 5 | 4 | | | 4 | 5 | |
| 5 | 8 | | | | | | | | | 5 | | 4 | | | 5 | 4 | 5 | | 5 | 5 | | 5 | | | | 3 | 5 | |
| | 4 | 1 | 2 | 1 | 1 | 3 | 4 | 2 | 3 | 3 | | 3 | 5 | | 3 | 3 | 4 | | 3 | 1 | | 2 | 2 | | | 3 | 3 | |
| | 2 | 1 | 1 | 1 | 1 | 1 | 3 | 1 | 2 | 1 | | 1 | 1 | | 1 | 1 | 4 | | 2 | 1 | | 1 | 1 | | | 2 | 3 | |
| | 1 | 1 | 1 | 1 | 1 | 1 | 1 | 1 | 1 | 1 | | 1 | 1 | | 1 | 1 | 3 | | 1 | 1 | | 1 | 1 | | | 1 | 1 | |
| 6 | 8 | | | | | | | | | 5 | | 5 | | | 5 | 5 | 5 | | 5 | 3 | | 5 | | | | 5 | 5 | |
| | 4 | 1 | 3 | 4 | 2 | 5 | 5 | 3 | 5 | 4 | | 4 | 5 | | 5 | 5 | 5 | | 5 | 2 | | 5 | 4 | | | 4 | 5 | |
| | 2 | 1 | 2 | 2 | 2 | 5 | 5 | 3 | 4 | 4 | | 4 | 5 | | 3 | 4 | 5 | | 4 | 2 | | 5 | 4 | | | 2 | 4 | |
| | 1 | 1 | 1 | 2 | 2 | 5 | 5 | 2 | 3 | 3 | | 3 | 5 | | 3 | 4 | 5 | | 3 | 1 | | 5 | 1 | | | 2 | 3 | |
| 7 | 8 | | | | | | | | | 5 | | 5 | | | 5 | 5 | 5 | | 5 | 5 | | 5 | | | | 5 | 5 | |
| | 4 | 1 | 3 | 1 | 1 | 4 | 5 | 3 | 5 | 5 | | 5 | 5 | | 4 | 5 | 5 | | 5 | 4 | | 5 | 4 | | | 3 | 5 | |
| | 2 | 1 | 3 | 1 | 1 | 4 | 4 | 3 | 4 | 4 | | 5 | 5 | | 3 | 4 | 5 | | 5 | 2 | | 5 | 4 | | | 2 | 5 | |
| | 1 | 1 | 2 | 1 | 1 | 4 | 4 | 2 | 4 | 4 | | 5 | 5 | | 1 | 3 | 4 | | 5 | 2 | | 4 | 3 | | | 1 | 4 | |
| 8 | 8 | | | 1 | | | | | | 1 | 1 | | | | 1 | 1 | 1 | | 1 | | | | | | | 2 | | |
| 9 | 8 | | | 1 | | | | | | 1 | 1 | | | | 3 | 2 | 4 | | 1 | | | | | | | 1 | | |
| 10 | 8 | | | 2 | | | | | | 1 | 2 | | | | 1 | 2 | 3 | | 1 | | | | | | | 2 | | |
| 11 | 8 | | | 1 | | | | | | 1 | 1 | | | | 1 | 1 | 1 | | 1 | | | | | | | 1 | | |
| 12 | 8 | | | 1 | | | | | | 1 | 1 | | | | 1 | 1 | 1 | | 1 | | | | | | | 1 | | |
| 13 | 8 | | | 1 | | | | | | 1 | 1 | | | | 1 | 1 | 1 | | 1 | | | | | | | 1 | | |

TABLE 3

| EX. No. | Rate lbs/A | A | B | C | D | E | F | G | H | I | J | K | L | M | N | O | P | Q | R | S | T | U | V | W | X | Y | Z | a |
|---|---|---|---|---|---|---|---|---|---|---|---|---|---|---|---|---|---|---|---|---|---|---|---|---|---|---|---|---|
| 1 | .5 | | | | | | | | | 5 | | 5 | | | 4 | 5 | 5 | | 5 | 5 | | 5 | | | | 5 | 5 | |
| | .5 | | | | | | | | | 5 | | 5 | | | 4 | 5 | 5 | | 5 | 4 | | 5 | | | | 4 | 5 | |
| | .2 | | | | | | | | | 5 | | 5 | | | 3 | 5 | 4 | | 5 | 4 | | 5 | | | | 4 | 5 | |
| | .2 | | | | | | | | | 5 | | 4 | | | 3 | 5 | 5 | | 4 | 3 | | 4 | | | | 4 | 5 | |
| | 8 | | | | | | | | | 5 | | 5 | | | 5 | 5 | 5 | | 5 | 5 | | 5 | | | | 5 | 5 | |
| | 4 | | | | | | | | | 5 | | 5 | | | 5 | 5 | 5 | | 5 | 5 | | 5 | | | | 5 | 5 | |
| | 2 | | | | | | | | | 5 | | 5 | | | 5 | 5 | 5 | | 5 | 5 | | 5 | | | | 5 | 5 | |
| | 1 | | | | | | | | | 5 | | 5 | | | 5 | 5 | 5 | | 5 | 5 | | 5 | | | | 5 | 5 | |
| | 1 | | | | | | | | | 5 | | 5 | | | 5 | 5 | 5 | | 5 | 5 | | 5 | | | | 5 | 5 | |
| | 1 | | | | | | | | | 5 | | 5 | | | 4 | 5 | 5 | | 5 | 4 | | 5 | | | | 4 | 5 | |
| 2 | .5 | | | | | | | | | 2 | | 2 | | | 2 | 4 | 4 | | 3 | 1 | | 3 | | | | 2 | 3 | |
| | .2 | | | | | | | | | 2 | | 1 | | | 1 | 3 | 4 | | 2 | 1 | | 2 | | | | 2 | 2 | |
| | 8 | | | | | | | | | 5 | | 5 | | | 5 | 5 | 5 | | 5 | 5 | | 5 | | | | 5 | 5 | |
| | 4 | | | | | | | | | 5 | | 4 | | | 4 | 5 | 5 | | 4 | 4 | | 5 | | | | 4 | 5 | |
| | 2 | | | | | | | | | 5 | | 4 | | | 2 | 5 | 5 | | 4 | 4 | | 5 | | | | 4 | 5 | |
| | 1 | | | | | | | | | 5 | | 3 | | | 2 | 5 | 5 | | 3 | 4 | | 4 | | | | 4 | 4 | |
| | 1 | | | | | | | | | 4 | | 3 | | | 2 | 4 | 4 | | 4 | 3 | | 4 | | | | 4 | 5 | |
| 3 | 8 | | | | | | | | | 2 | | 1 | | | 1 | 4 | 5 | | 3 | 2 | | 3 | | | | 3 | 3 | |
| | 4 | | | | | | | | | 2 | | 1 | | | 1 | 2 | 3 | | 2 | 1 | | 3 | | | | 1 | 2 | |
| | 2 | | | | | | | | | 1 | | 1 | | | 1 | 1 | 2 | | 2 | 1 | | 2 | | | | 1 | 2 | |
| | 1 | | | | | | | | | 1 | | 1 | | | 1 | 1 | 2 | | 1 | 1 | | 1 | | | | 1 | 1 | |
| 4 | 8 | | | | | | | | | 5 | | 5 | | | 5 | 5 | 5 | | 5 | 5 | | 5 | | | | 5 | 5 | |
| | 4 | | | | | | | | | 5 | | 5 | | | 4 | 4 | 5 | | 4 | 4 | | 4 | | | | 4 | 4 | |
| | 2 | | | | | | | | | 5 | | 3 | | | 3 | 4 | 5 | | 4 | 4 | | 4 | | | | 4 | 4 | |
| | 1 | | | | | | | | | 4 | | 3 | | | 2 | 4 | 5 | | 3 | 3 | | 4 | | | | 3 | 3 | |
| 5 | 8 | | | | | | | | | 4 | | 2 | | | 2 | 4 | 4 | | 2 | 1 | | 4 | | | | 3 | 3 | |
| | 4 | | | | | | | | | 2 | | 1 | | | 1 | 3 | 4 | | 1 | 1 | | 3 | | | | 3 | 2 | |
| | 2 | | | | | | | | | 1 | | 1 | | | 1 | 2 | 2 | | 1 | 1 | | 2 | | | | 2 | 2 | |
| | 1 | | | | | | | | | 1 | | 1 | | | 1 | 1 | 2 | | 1 | 1 | | 3 | | | | 1 | 2 | |
| 6 | 8 | | | | | | | | | 4 | | 3 | | | 5 | 5 | 5 | | 5 | 4 | | 5 | | | | 4 | 4 | |
| | 4 | | | | | | | | | 4 | | 2 | | | 2 | 4 | 5 | | 3 | 1 | | 4 | | | | 3 | 2 | |
| | 2 | | | | | | | | | 2 | | 2 | | | 1 | 4 | 5 | | 3 | 1 | | 4 | | | | 2 | 2 | |
| | 1 | | | | | | | | | 2 | | 1 | | | 1 | 3 | 4 | | 2 | 1 | | 3 | | | | 2 | 2 | |
| 7 | 8 | | | | | | | | | 5 | | 5 | | | 5 | 5 | 5 | | 5 | 5 | | 5 | | | | 4 | 5 | |
| | 4 | | | | | | | | | 5 | | 4 | | | 3 | 4 | 5 | | 5 | 4 | | 5 | | | | 4 | 5 | |
| | 2 | | | | | | | | | 5 | | 4 | | | 2 | 4 | 5 | | 4 | 4 | | 4 | | | | 4 | 4 | |
| | 1 | | | | | | | | | 5 | | 3 | | | 2 | 4 | 4 | | 4 | 4 | | 4 | | | | 4 | 4 | |
| 8 | 8 | | 1 | | | | | | | 1 | 1 | | | | 1 | 1 | 1 | | 1 | | | | | | | 1 | | |
| 9 | 8 | | 1 | | | | | | | 1 | 1 | | | | 1 | 2 | 3 | | 1 | | | | | | | 1 | | |
| 10 | 8 | | 2 | | | | | | | 1 | 1 | | | | 1 | 1 | 3 | | 1 | | | | | | | 2 | | |
| 11 | 8 | | 1 | | | | | | | 1 | 1 | | | | 1 | 1 | 1 | | 1 | | | | | | | 1 | | |
| 12 | 8 | | 1 | | | | | | | 1 | 1 | | | | 1 | 1 | 1 | | 1 | | | | | | | 1 | | |

TABLE 3-continued

| EX. No. | Rate lbs/A | PLANT SPECIES Post-emergence | | | | | | | | | | | | | | | | | | | | | | | | | |
|---|---|---|---|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | U | V | W | X | Y | Z | a |
| 13 | 8 | 1 | | | | | | | | 1 | 1 | | | | 1 | 1 | 1 | | 1 | | | | | | | | | 1 |

Some of the compounds of this invention were further tested as described above. In addition to some of the species listed above, the compounds were evaluated against: Sorghum, Nightshade, Buckweed, and Sicklepod.

In addition to the code used above, the following code was used:
b=Sorghum
c=Nightshade
d=Buckweed
e=Sicklepod The compounds were pre-plant incorporated (PPI) or surface applied (SA). Plant injury ratings were made visually on a scale of 0–10 with 0 being no injury and 10 being plant death. The injury rating was multiplied by 10 to obtain a percent inhibition.

The results are recorded in Tables 4 and 5.

amount will depend upon a number of factors, including the method of application, formulation, soil texture, soil moisture content, the expected population of unwanted vegetation, degree of incorporation, the extent of growth control desired, and related factors. The rate of application normally will be from about 0.01 to about 10.0 pounds per acre, and preferably from about 0.25 to about 5.0 pounds per acre. These ranges are equivalent, respectively, to from about 0.011 to about 11.2 kilograms per hectare, and from about 0.28 to about 5.6 kilograms per hectare.

TERRESTRIAL HERBICIDAL FORMULATIONS

The compounds of the present invention may also be formulated with a suitable agriculturally-acceptable carrier. Such compositions will contain from about 5 to about 95.0 percent by weight of the active ingredient,

TABLE 4

PREEMERGENCE HERBICIDE TESTING
PERCENT CROP INJURY OR WEED CONTROL

| EX. No. | lb/A | APP. | A | b | D | G | S | K | U | C | B | P | Z | W | X | c |
|---|---|---|---|---|---|---|---|---|---|---|---|---|---|---|---|---|
| 1 | .06 | PPI | 0 | 0 | 80 | 60 | 40 | 60 | 98 | 20 | 0 | 90 | 80 | 100 | 100 | 100 |
| | .12 | PPI | 30 | 40 | 100 | 98 | 100 | 98 | 100 | 70 | 40 | 100 | 100 | 100 | 100 | 100 |
| | .25 | PPI | 30 | 80 | 100 | 100 | 100 | 100 | 100 | 100 | 100 | 100 | 100 | 100 | 100 | 100 |
| | .25 | PPI | 50 | 98 | 100 | 100 | 100 | 100 | 100 | 100 | 95 | 100 | 100 | 100 | 100 | 100 |
| | .50 | PPI | 80 | 100 | 100 | 100 | 100 | 100 | 100 | 100 | 100 | 100 | 100 | 100 | 100 | 100 |
| | 1.00 | PPI | 80 | 80 | 100 | 100 | 100 | 100 | 100 | 100 | 100 | 100 | 100 | 100 | 100 | 100 |
| | .06 | SA | 0 | 0 | 0 | 0 | 50 | 0 | 0 | 0 | 0 | 80 | 0 | 80 | 60 | 80 |
| | .12 | SA | 0 | 0 | 30 | 30 | 100 | 80 | 10 | 10 | 0 | 100 | 50 | 100 | 100 | 100 |
| | .25 | SA | 20 | 50 | 50 | 90 | 100 | 100 | 90 | 95 | 40 | 100 | 98 | 100 | 100 | 100 |
| | .25 | SA | 30 | 40 | 40 | 40 | 100 | 95 | 50 | 90 | 10 | 100 | 95 | 100 | 80 | 100 |
| | .50 | SA | 50 | 60 | 40 | 98 | 100 | 100 | 98 | 100 | 90 | 100 | 98 | 100 | 100 | 100 |
| | 1.00 | SA | 60 | 98 | 80 | 100 | 100 | 100 | 100 | 100 | 100 | 100 | 100 | 100 | 100 | 100 |
| 2 | .25 | PPI | 0 | 0 | 0 | 20 | 20 | 30 | 10 | 0 | 10 | 95 | 20 | 40 | 80 | 100 |
| | .50 | PPI | 0 | 0 | 10 | 40 | 80 | 50 | 60 | 10 | 30 | 100 | 80 | 90 | 98 | 100 |
| | 1.00 | PPI | 0 | 0 | 30 | 60 | 100 | 80 | 80 | 40 | 70 | 100 | 100 | 100 | 100 | 100 |
| | .50 | SA | 0 | 0 | 0 | 30 | 95 | 80 | 10 | 0 | 10 | 100 | 30 | 100 | 100 | 100 |
| | 1.00 | SA | 20 | 0 | 0 | 30 | 100 | 90 | 10 | 10 | 30 | 100 | 60 | 100 | 100 | 100 |
| | 2.00 | SA | 20 | 20 | 0 | 50 | 100 | 100 | 40 | 50 | 60 | 100 | 80 | 100 | 100 | 100 |

TABLE 5

POSTEMERGENCE HERBICIDE TESTING
PERCENT CROP INJURY OR WEED CONTROL

| EX. No. | lb/A | A | b | G | K | D | U | S | N | B | C | F | d | X | Z | O | c | P | e | W | a |
|---|---|---|---|---|---|---|---|---|---|---|---|---|---|---|---|---|---|---|---|---|---|
| 1 | .06 | 0 | 10 | 50 | 60 | 30 | 30 | 90 | 80 | 40 | 70 | 100 | 0 | 80 | 70 | 90 | 90 | 80 | 50 | 70 | 80 |
| | .12 | 0 | 10 | 50 | 95 | 40 | 50 | 90 | 80 | 60 | 90 | 100 | 50 | 90 | 90 | 98 | 95 | 80 | 80 | 90 | 100 |
| | .25 | 0 | 30 | 20 | 95 | 10 | 50 | 100 | 80 | 95 | 70 | 100 | 50 | 100 | 50 | 98 | 100 | 90 | 98 | 90 | 100 |
| | .25 | 0 | 20 | 60 | 95 | 40 | 80 | 100 | 80 | 60 | 90 | 100 | 80 | 95 | 95 | 98 | 95 | 98 | 90 | 95 | 100 |
| | .50 | 0 | 30 | 100 | 100 | 100 | 100 | 100 | 98 | 50 | 40 | 100 | 20 | 100 | 98 | 98 | 100 | 100 | 30 | 98 | 95 |
| | 1.00 | 10 | 90 | 80 | 100 | 50 | 100 | 100 | 100 | 100 | 98 | 100 | 100 | 100 | 95 | 100 | 100 | 100 | 100 | 100 | 100 |
| 2 | .50 | 0 | 0 | 0 | 60 | 0 | 0 | 40 | 10 | 10 | 10 | 90 | 50 | 0 | 20 | 80 | 95 | 98 | 30 | 50 | 60 |
| | 1.00 | 0 | 10 | 30 | 80 | 0 | 30 | 80 | 10 | 40 | 20 | 80 | 70 | 20 | 50 | 90 | 100 | 98 | 30 | 80 | 60 |
| | 2.00 | 40 | 50 | 50 | 100 | 10 | 70 | 100 | 50 | 80 | 50 | 100 | 80 | 98 | 90 | 95 | 100 | 100 | 90 | 95 | 98 |
| 4 | .50 | 0 | 0 | 40 | 80 | 10 | 60 | 60 | 70 | 60 | 50 | 98 | 60 | 50 | 80 | 80 | — | 100 | 98 | 95 | 40 |
| | 1.00 | 0 | 30 | 60 | 80 | 60 | 80 | 70 | 90 | 80 | 80 | 100 | 100 | 60 | 80 | 95 | — | 100 | 100 | 98 | 80 |
| | 2.00 | 30 | 60 | 80 | 80 | 70 | 98 | 98 | 90 | 98 | 80 | 100 | 100 | 98 | 90 | 100 | — | 100 | 100 | 98 | 98 |
| 6 | 1.00 | 0 | 0 | 0 | 0 | 0 | 0 | 0 | 0 | 70 | 30 | 60 | 50 | 0 | 30 | 30 | 0 | 90 | 20 | 50 | 0 |
| | 2.00 | 0 | 0 | 10 | 0 | 0 | 0 | 0 | 0 | 90 | 50 | 80 | 95 | 0 | 50 | 70 | 20 | 90 | 40 | 80 | 30 |
| | 4.00 | 10 | 50 | 50 | 30 | 0 | 0 | 10 | 0 | 90 | 60 | 95 | 95 | 0 | 80 | 100 | 60 | 98 | 100 | 95 | 60 |

The amount of herbicidal pyridinylimidazolidinones to be employed in the method of this invention is an amount, which is effective in controlling or inhibiting the growth or unwanted vegetation. Such herbicidal depending on the composition desired. Sprayable formulations are preferred, because of the rapidity and economy of application, and because the sprayed applications do not drift to untreated areas as would a dust, for example.

The most convenient formulations are in the form of concentrated compositions to be applied by spraying as water dispersions or emulsions containing in the range from about 0.1 percent to about 10 percent of the compounds. Water-dispersible or emulsifiable compositions may be either solids usually known as wettable powders, or liquids usually known as emulsifiable concentrates.

A typical wettable powder comprises an intimate mixture of a compound of the invention, an inert carrier, and surfactants. The concentration of the active compound is usually from about 25 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent by weight of the wettable powder, are chosen from among the sulfonated lignins, the condensed napthalenesulfonates, and the alkyl sulfates.

A typical emulsifiable concentrate comprises from about 1 to about 6 pounds of a compound of the invention per gallon of liquid, dissolved in a mixture of organic solvents and emulsifiers. The organic solvent is chosen with regard to its solvency and its cost. Useful solvents include the aromatics, especially the xylenes and the heavy aromatic naphthas. Hydrophilic cosolvents such as cyclohexanone and isophorone may be included. Other organic solvents may also be used, including the terpenic solvents and kerosene. Suitable emulsifiers for emulsifiable concentrates are chosen from the alkylbenzenesulfonates, napthalenesulfonates, and nonionic surfactants such as alkylphenol adducts of polyoxyethylene, and are used at similar percentages as for wettable powders.

The compounds of this invention may be formulated as flowables or aqueous suspensions. A typical flowable formulation contains from about 12 to 75% by weight of the active ingredient, surfactants which are wetting and dispersing agents of the types used in wettable powder formulations and used at from 1 to 10 percent, about 5 to 10% of an antifreeze solution such as ethylene or propylene glycol, and a bulking or thickening agent. These thickeners may be natural water soluble gums, clays with gelling properties, cellulose derivatives and the like, and are used from about 0.5% to 5% of the product. The remainder of the formula is water. The product is prepared by grinding the slurry in a ball mill or sand mill to the desired particle size. Antifoam compounds, usually of the silicone type, may be added at 0.05% to 1% to control product foaming.

Solid, granular compositions are convenient for the application of compounds of this invention to the soil and will contain the active agent in an amount from about 0.1 to about 20% by weight. Granules comprise a compound of the invention dispersed on a granular inert carrier such as coarsely ground clay of from about 0.1 to about 3 mm particle size. The compound is most conveniently applied to the clay by dissolving it in an inexpensive solvent and applying the solution to the sized clay in an appropriate solids mixer.

The formulated compounds are applied to plants in the manners conventional in agricultural chemistry. Sprayable compositions are easily applied by any of many types of sprayers available to the art. Self-propelled, tractor-mounted, and towed spray devices which apply the water-dispersed formulations through calibrated atomizing nozzles are available and effective. Metering applicators are also available which can apply accurately measured quantities of granular compositions to the soil. The operator of the application equipment need only take care to adjust the equipment to apply an amount of the water-dispersed or granular formulation per acre which supplies the desired application rate of the compound, and to apply the amount uniformly to the plants to be treated.

The following detailed examples of formulations illustrate preferred aspects of the invention.

| Emulsifiable Concentrate (1EC) | |
|---|---|
| Ingredient | Percent by weight |
| Compound of Example 1 | 12.9 |
| Toximul H, a blend of emulsifiers, from Stepan Chemical Co. | 10.0 |
| Dowanol PM, propylene glycol monomethyl ether, from Dow Chemical Co. | 15.0 |
| Heavy Aromatic Naphtha | 62.1 |
| | 100.0 |

The above ingredients are blended together to form the concentrate.

| Aqueous Suspension (1 lb/gal) | |
|---|---|
| Ingredient | Percent by weight |
| Compound of Example 1 | 12.1 |
| Tergitol TMN-6, wetting agent, from Union Carbide | 10.0 |
| Polyfon H, a dispersant, from Westvaco Corp. | 0.5 |
| Propylene glycol | 10.0 |
| Xanthan gum, a thickening agent, from Kelco Co. | 1.0 |
| Antifoam C, a foam suppressant, from Dow Corning | 0.5 |
| Water | 65.9 |
| | 100.0 |

The soluble components and water are added to a tank equipped with a high shear mixer. The compound is added and mixed in. The mixture is circulated through a liquid grinding mill until the desired particle size is attained. Prehydrated xanthan gum is then added.

| Granule | |
|---|---|
| Ingredient | Percent by weight |
| Compound of Example 1 | 5.0 |
| Clay granule | 95.0 |
| | 100.0 |

The compound is substantially dissolved in acetone or similar solvent, and the organic solution is sprayed onto the clay, which is in the form of granules. The mixture is then thoroughly blended and the solvent removed by drying.

| Wettable Powder | |
|---|---|
| Ingredient | Percent by weight |
| Compound of Example 1 | 75.0 |
| Fuller's earth | 19.0 |
| Sulfonated lignin | 3.5 |
| Sodium lauryl sulfate | 2.5 |

| Wettable Powder | |
|---|---|
| Ingredient | Percent by weight |
| | 100.0 |

The above ingredients are blended to uniformity and are ground in a hammer mill or air mill. The product is then reblended to a homogeneous free-flowing powder. The powder is dispersed in water and sprayed onto the weed-infested area.

We claim:

1. A compound of the formula (I)

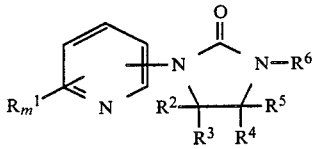

wherein
$R^1$ is halogen, $C_1$-$C_6$ alkyl, or halo($C_1$-$C_6$ alkyl);
$R^2$ is hydrogen, hydroxy, or

wherein
$R^7$ is $C_1$-$C_6$ alkyl or

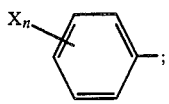

X is halogen, $C_1$-$C_6$ alkyl, $C_1$-$C_6$ alkoxy, or halo($C_1$-$C_6$ alkyl);

$R^3$ is hydrogen or $C_1$-$C_6$ alkyl;
$R^4$ is hydrogen or hydroxy;
$R^5$ is hydrogen or $C_1$-$C_6$ alkyl;
$R^6$ is hydrogen or $C_1$-$C_6$ alkyl; and
m and n are integers from 0 to 2.

2. The compound of claim 1 wherein
$R^1$ is halogen or $C_1$-$C_4$ alkyl;
$R^2$ is hydroxy;
$R^3$, $R^4$, and $R^5$ are hydrogen; and
$R^6$ is methyl.

3. The compound of claim 2 which is 3-[4-(1,1-dimethylethyl)-2-pyridinyl]-4-hydroxy-1-methyl-2-imidazolidinone.

4. The compound of claim 2 which is 3-(5-chloro-2-pyridinyl)-4-hydroxy-1-methyl-2-imidazolidinone.

5. The compound of claim 2 which is 4-hydroxy-3-(4-methyl-2-pyridinyl)-1-methyl-2-imidazolidinone.

6. The compound of claim 2 which is 3-(5-bromo-2-pyridinyl)-4-hydroxy-1-methyl-2-imidazolidinone.

7. A formulation comprising a compound of claim 1 together with an agriculturally-acceptable carrier therefor.

8. The formulation of claim 7 wherein
$R^1$ is halogen or $C_1$-$C_4$ alkyl;
$R^2$ is hydroxy;
$R^3$, $R^4$, and $R^5$ are hydrogen; and
$R^6$ is methyl.

9. The formulation of claim 8 wherein the compound is 3-[4-(1,1-dimethylethyl)-2-pyridinyl]-4-hydroxy-1-methyl-2-imidazolidinone.

10. The formulation of claim 8 wherein the compound is 3-(5-chloro-2-pyridinyl)-4-hydroxy-1-methyl-2-imidazolidinone.

11. The formulation of claim 8 wherein the compound is 4-hydroxy-3-(4-methyl-2-pyridinyl)-1-methyl-2-imidazolidinone.

12. The formulation of claim 8 wherein the compound is 3-(5-bromo-2-pyridinyl)-4-hydroxy-1-methyl-2-imidazolidinone.

* * * * *